United States Patent
Gentempo, Jr. et al.

(10) Patent No.: US 7,438,466 B2
(45) Date of Patent: Oct. 21, 2008

(54) CALIBRATING A THERMAL SCANNING SYSTEM

(76) Inventors: Patrick Gentempo, Jr., 22 Overlook Ridge, Oakland, NJ (US) 07436; Lee L Brody, 120 Pearson Rd., Somerville, MA (US) 02144

( * ) Notice: Subject to any disclaimer, the term of this patent is extended or adjusted under 35 U.S.C. 154(b) by 111 days.

(21) Appl. No.: 11/615,875

(22) Filed: Dec. 22, 2006

(65) Prior Publication Data
US 2007/0147464 A1 Jun. 28, 2007

Related U.S. Application Data

(60) Provisional application No. 60/753,109, filed on Dec. 22, 2005.

(51) Int. Cl.
G01K 15/00 (2006.01)
G01K 13/00 (2006.01)
G01K 3/00 (2006.01)
G01J 5/00 (2006.01)
A61B 5/00 (2006.01)

(52) U.S. Cl. .......................... 374/1; 374/112; 374/167; 374/137; 374/124; 600/549; 600/474

(58) Field of Classification Search .............. 374/1, 374/112, 137, 124, 167; 600/474, 549
See application file for complete search history.

(56) References Cited

U.S. PATENT DOCUMENTS

| 2,297,868 | A | * | 10/1942 | Bergeron | 374/114 |
| 3,980,073 | A | * | 9/1976 | Shaw, IV | 600/547 |
| 4,347,854 | A | * | 9/1982 | Gosline et al. | 600/549 |
| 5,060,657 | A | * | 10/1991 | Teague | 600/549 |
| 6,539,328 | B1 | * | 3/2003 | Cremonese et al. | 702/151 |
| 7,115,098 | B2 | * | 10/2006 | Gentempo et al. | 600/549 |

* cited by examiner

*Primary Examiner*—Edward Lefkowitz
*Assistant Examiner*—Mirellys Jagan
(74) *Attorney, Agent, or Firm*—Knobbe, Martens, Olson & Bear, LLP (57) ABSTRACT

A method for recalibrating a bilateral thermal scanner comprising a first thermal sensor and a second thermal sensor can comprise acquiring a first set of thermal scanning data with the thermal sensors in their normal positions; optionally analyzing the first set of thermal scanning data is analyzed to determine if the data has a one-sided bias; acquiring a second set of thermal scanning data with the positions of the thermal sensors reversed; determining a calibration from the first and second sets of thermal scanning data; and optionally correcting at least one of the first and/or second set of thermal scanning data using the calibration.

18 Claims, 5 Drawing Sheets

CALIBRATING A THERMAL SCANNING SYSTEM

CROSS-REFERENCE TO RELATED APPLICATIONS

This application claims the benefit of U.S. Application No. 60/753,109, filed Dec. 22, 2005, the disclosure of which is incorporated by reference.

BACKGROUND

1. Technical Field

This disclosure generally relates to a method for calibrating medical diagnostic equipment, and more particularly, to a method for calibrating a thermal scanning system.

2. Description of the Related Art

Chiropractors and other health care professionals currently use devices to measure skin temperature at a variety of locations along a patient's spinal column. The purpose of taking such measurements is to monitor skin temperatures surrounding the spine. Imbalances in bilateral skin temperature readings may be indicative of abnormal autonomous nervous system activity, which in turn may indicate a spinal subluxation, or misalignment of adjacent vertebrae. Chiropractic care is directed toward locating and correcting subluxations by spinal adjustment. By creating a record of thermal readings paraspinally, i.e., along both left and right sides of a patient's spine, during the course of care, a chiropractor can quantitatively assess where subluxations exist, and how chiropractic care helps to alleviate them.

There are many commercially available medical devices capable of recording bi-lateral skin temperatures. One variety of these instruments utilizes two or more infrared thermal sensors mounted in a hand held unit which is rolled along a patient's spine. Two commercially available examples of such instruments are the "Insight Millennium Rolling Thermal Scanner" (Chiropractic Leadership Alliance, Mahwah, N.J.) and the "TyTron C-3000" (Titronics Research & Development, Oxford, Iowa).

In order to determine temperature imbalances along the spine, these instruments are rolled along the spine, and individual infrared thermal sensors independently measure the temperature on either side of the spine. Temperature differences of a few tenths of a degree Fahrenheit and/or Celsius are often considered clinically significant by clinicians.

The lynchpin in the theory of associating recorded temperature differences with actual skin temperature differences is the assumption that the two independent thermal sensors are precisely calibrated to one another throughout the full range of temperature readings. This is often not the case in practice, however, as the calibration of each of the thermal sensors can drift over time or be influenced by environmental conditions such as operating temperature and humidity.

In the real world, the clinicians who use these systems often must ask the question: "Is the measured temperature bilateral difference merely a result of calibration differences between adjacent sensors?" There are currently two principal field calibration techniques, which are described below with reference to the commercially available devices identified above.

The Insight Millennium Rolling Thermal Scanner uses a "synchronization" function in which the user separately points each of the two thermal sensors at a stable temperature source such as an easily identified location on a patient's back. Once each sensor is pointed that the exact same location, any differences in the sensor readings are automatically calculated as adjustments in the software calibration values. Disadvantages of this technique include: (1) potential error in having the user point each sensor at a spot with a stable temperature reading, and (2) potentially collecting data from patients using sensors that are not calibrated.

The Tytron C-3000 uses a calibration procedure in which the user modifies the calibration of the sensors by manually adjusting the software calibration values based on observations of repeated imbalances in that temperature data. Disadvantages of this technique include: (1) lack of an objective measurement basis to alter the calibration values, and (2) the likelihood of data collection from patients using sensors that have not been recently calibrated. The calibration method is also confusing, as illustrated by the portion of the instructions for a "Minor Calibration, Field Adjustment Procedure" taken from the Tytron C-3000 User Guide set forth below:

> If the center graph (delta-T) readings seem to fall consistently to one side of the centerline the following adjustment in the scale factor for the opposite side will bring balance to zero. (If, for example, the scans seem to be slightly more to the right of the centerline, we would increase the temperature reading of the left probe to pull the average back to center.)
> 
> Scale Factors: Channel 0=calibration of LEFT barrel; Channel 2=calibration of RIGHT barrel
> 
> REDUCING the calibration number of the desired channel will INCREASE the temperature reading of that channel. REDUCING the number by 25 for example will increase the displayed temperature by approx. 0.5 degrees C.
> 
> EXAMPLE: If the center graph scans were all falling a bit to the left of center, we would want to increase the right probe's gain. We would therefore DECREASE the above scale factor for channel 2, thereby in-creasing the temperature of the right DT and "pull" the center reading towards centerline. For a small shift, subtract 10 from the example above and make channel 2's scale factor 1040. You may need to repeat this trial and error procedure after scanning 5 or 6 more patients and either take away more or add some back to bring balance to the center graph. A warning will appear when an attempt is made to change these settings, just click on "ok".

Thus, a need exists for a simple, easy to use, thermal calibration protocol and calculation in which the relative calibration of the two thermal sensors can be verified each time the system is utilized with a patient.

SUMMARY OF THE INVENTION

Embodiments of the present inventions relate to an improved thermal scanning calibration protocol and calculation. Some of the embodiments of the present inventions provide a more accurate and repeatable method of calibrating thermal sensors in the field. This can be accomplished by averaging several hundred data points to generate a robust measurement, which can eliminate the scenario in which patient data is collected with uncalibrated sensors. Additionally, the need for the user to determine when to perform a calibration procedure can be eliminated.

Accordingly, some embodiments disclosed herein provide a method for calibrating a bilateral thermal scanner comprising a first thermal sensor and a second thermal sensor, the method comprising: acquiring a first set of bilateral temperature data; determining whether the first set of bilateral temperature data has a one-sided bias; acquiring a second set of bilateral temperature data, wherein the positions of the first thermal sensor and second thermal sensor are substantially interchanged; and comparing the first and second sets of bilateral temperature data to determine a calibration for the bilateral thermal scanner.

Other embodiments provide a method for calibrating a bilateral thermal scanner comprising a first thermal sensor and a second thermal sensor, the method comprising: acquiring a first set of bilateral temperature data; acquiring a second set of bilateral temperature data, wherein the positions of the first thermal sensor and second thermal sensor are substantially interchanged; and comparing the first and second sets of bilateral temperature data to determine a calibration for the bilateral thermal scanner.

Further embodiments provide a method for performing a bilateral temperature measurement using a bilateral thermal scanner comprising a first thermal sensor and a second thermal sensor, the method comprising: acquiring a first set of bilateral temperature data; acquiring a second set of bilateral temperature data, wherein the positions of the first thermal sensor and second thermal sensor are substantially interchanged; comparing the first and second sets of bilateral temperature data to determine a calibration for the bilateral thermal scanner; and using the calibration to correct at least one of the first and second sets of bilateral temperature data.

Still further embodiments provide a method for performing a bilateral temperature measurement using a bilateral thermal scanner comprising a first thermal sensor and a second thermal sensor, the method comprising: acquiring a first set of bilateral temperature data; acquiring a second set of bilateral temperature data, wherein the positions of the first thermal sensor and second thermal sensor are substantially interchanged; and calculating a bilateral temperature measurement from the first and second sets of bilateral temperature data.

Other embodiments provide a method for calibrating a bilateral thermal, the method comprising: acquiring, with a bilateral thermal scanner comprising a first thermal sensor and a second thermal sensor, a first set of bilateral temperature data using the first thermal sensor and the second thermal sensor; acquiring a second set of bilateral temperature data, wherein the positions of the first thermal sensor and second thermal sensor are substantially interchanged; and comparing the first and second sets of bilateral temperature data to determine at least one calibration value for the bilateral thermal scanner.

In some embodiments, the acquiring step involves rolling the bilateral thermal scanner over a surface. In some embodiments, the acquiring step involves placing the first and second thermal sensors, which are operable to determine temperature, against a surface. Some embodiments further comprise activating a component of the bilateral thermal scanner to initiate data acquisition. In some embodiments, the acquiring step involves placing the first and second thermal sensors to collect thermal data from opposite sides of a patient's spine. In some embodiments, the acquiring step involves sensing the intensity of radiation. Some embodiments further comprise displaying at least some of the acquired bilateral temperature data.

Some embodiments further comprise determining whether the first set of bilateral temperature data has a one-sided bias. In some embodiments, determining whether the first set of bilateral temperature data has a one-sided bias comprises calculating a difference between an average of temperature data from the first thermal sensor and an average of temperature data from the first thermal sensor. Some embodiments further comprise prompting a user to perform a calibration test if the one-sided bias is greater than a predetermined value.

In some embodiments, one of acquiring a first set of bilateral temperature data and acquiring a second set of bilateral temperature data comprises scanning up a patient's spine, and the other of acquiring a first set of bilateral temperature data and acquiring a second set of bilateral temperature data comprises scanning down a patient's spine.

In some embodiments, the at least one calibration value comprises at least one of a gain and an offset. Some embodiments further comprise applying the at least one calibration value to at least one of the first and second sets bilateral temperature data. Some embodiments further comprise applying the at least one calibration value to the output of at least one of the first and second thermal sensors. Some embodiments further comprise saving the at least one calibration value. In some embodiments, the at least one calibration value is applied to a subsequent set of bilateral temperature data.

Other embodiments provide a method for performing a bilateral temperature measurement using a bilateral thermal scanner comprising a first thermal sensor and a second thermal sensor, the method comprising: acquiring a first set of bilateral temperature data using bilateral thermal scanner; acquiring a second set of bilateral temperature data, wherein the positions of the first thermal sensor and second thermal sensor are substantially interchanged; and calculating a bilateral temperature measurement from the first and second sets of bilateral temperature data.

Other embodiments provide a system for calibrating a bilateral thermal scanner comprising: a bilateral thermal scanner comprising a first thermal sensor and a second thermal sensor; a display; a data processing unit coupled to the bilateral thermal scanner and the display; and machine readable instructions. The machine readable instructions when executed on the data processing unit calibrate the bilateral thermal scanner by a method comprising: comparing a first set of bilateral temperature data and a second set of bilateral temperature data to determine at least one calibration value for the bilateral thermal scanner, wherein the positions of the first thermal sensor and the second thermal sensor are substantially interchanged between acquiring the first set of bilateral temperature data and the second set of bilateral temperature data.

BRIEF DESCRIPTION OF THE DRAWINGS

These and other features, aspects and advantages of the present inventions will now be described in connection with preferred embodiments, in reference to the accompanying drawings. The illustrated embodiments, however, are merely examples and are not intended to limit the invention. The drawings include the following 5 figures.

DETAILED DESCRIPTION OF PREFERRED EMBODIMENTS

Described herein are embodiments including methods and systems for calibrating a device for measuring and/or recording bilateral skin temperatures. The following description refers to the Insight Millennium Rolling Thermal Scanner ("Rolling Thermal Scanner"), but those skilled in the art will understand that the method is applicable to other bilateral thermal scanners, as well as to other scanners with more than two thermal sensors.

The Rolling Thermal Scanner comprises a first or left thermal sensor, and a second or right thermal sensor. Typically, the Rolling Thermal Scanner is positioned at the base of a patient's spine, and rolled to the top spine. As the scanner moves up the patient's spine, the left thermal sensor collects thermal data from the left side of the patient's body, and the right thermal sensor collects thermal data from the right side of the patient's body. The Rolling Thermal Scanner also optionally comprises one or more user input devices, for example buttons and/or triggers that are used, for example, to initiate and/or terminate data acquisition. In some embodiments, the Rolling Thermal Scanner also includes outputs, for example, lights, a display, and/or a speaker used to provide the user with information, for example, the condition of the scanner, instructions to the user, and/or diagnostic information.

The first and second thermal sensors are typically infrared detectors disposed on the thermal scanner with a predetermined horizontal spacing therebetween. Typically, the left and right thermal sensors in a thermal scanner are factory calibrated so that the outputs of the left and right sensor channels are balanced: that is, the outputs of the channels are adjusted to be the same for the same skin temperature. The calibration is typically performed using software, however, those skilled in the art will appreciate that other means for calibration are also possible, for example, electronically. With time, however, the left and right channels often become unbalanced, for example, because of differential drift between the sensors, physical wear and tear, and the like. The thermal scanner is then recalibrated, for example, as discussed above. In some embodiments, the gains of the left and/or right channels are adjusted in the recalibration. In other embodiments, one or more offsets are applied to the left and/or right channels. Other embodiments apply one or more gain adjustments and offsets to the left and/or right channels.

Figure 1:
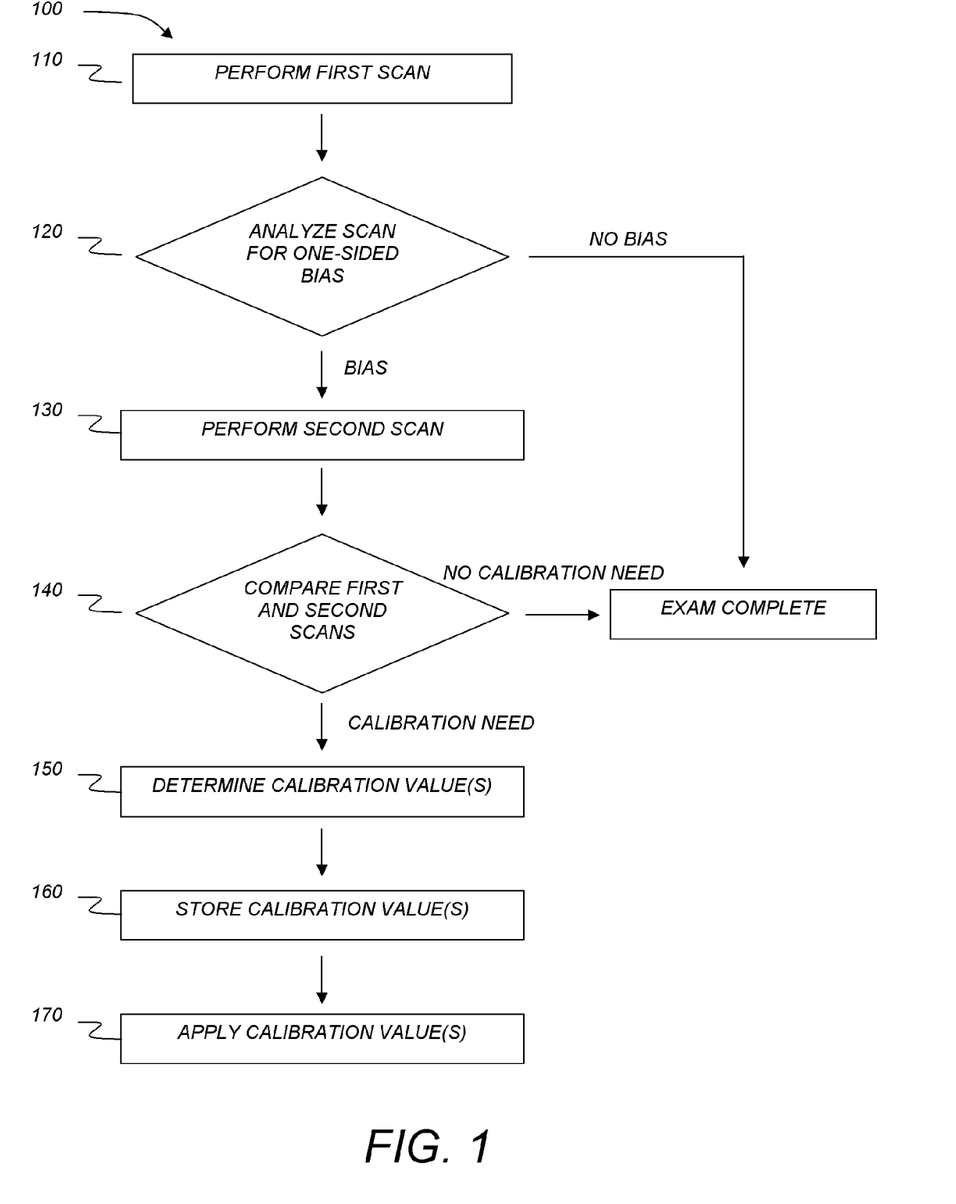
FIG. 1 is a flowchart illustrating an embodiment of a method for calibrating a bilateral thermal scanner in accordance with a preferred embodiment of the present invention.

FIG. 1 is a flow chart illustrating an embodiment 100 of a calibration method. In step 110, a first set of thermal scanning data is acquired with the thermal sensors in their normal positions. In optional step 120, the first set of thermal scanning data is analyzed to determine if the data has a one-sided bias. If there is no one-sided bias, the examination is complete. If a one-sided bias is detected, the user is prompted to perform a calibration test in step 130.

In the calibration test of step 130, a second set of thermal scanning data is acquired with the positions of the thermal sensors reversed. In step 140, the first and second sets of thermal calibration data are compared to determine if the thermal scanner needs calibration. If the thermal scanner does not require calibration, the examination is complete.

In step 150, calibration values are determined from the first and second set of thermal scanning data. In step 160, the calibration values are stored. In step 170, at least one of the first and/or second set of thermal scanning data is corrected using the calibration and the corrected data are stored.

In step 110, a first set of thermal scanning data is collected. In the illustrated embodiment, skin temperature data is collected bilaterally along the spine. In some exemplary embodiments, a Rolling Thermal Scanner is positioned at the base of the spine, and the user waits for an on-screen indicator that the skin temperature readings are stable. Once the readings are stable, the user slowly rolls the thermal scanner up the spine to the top of the spine.

Figure 2:
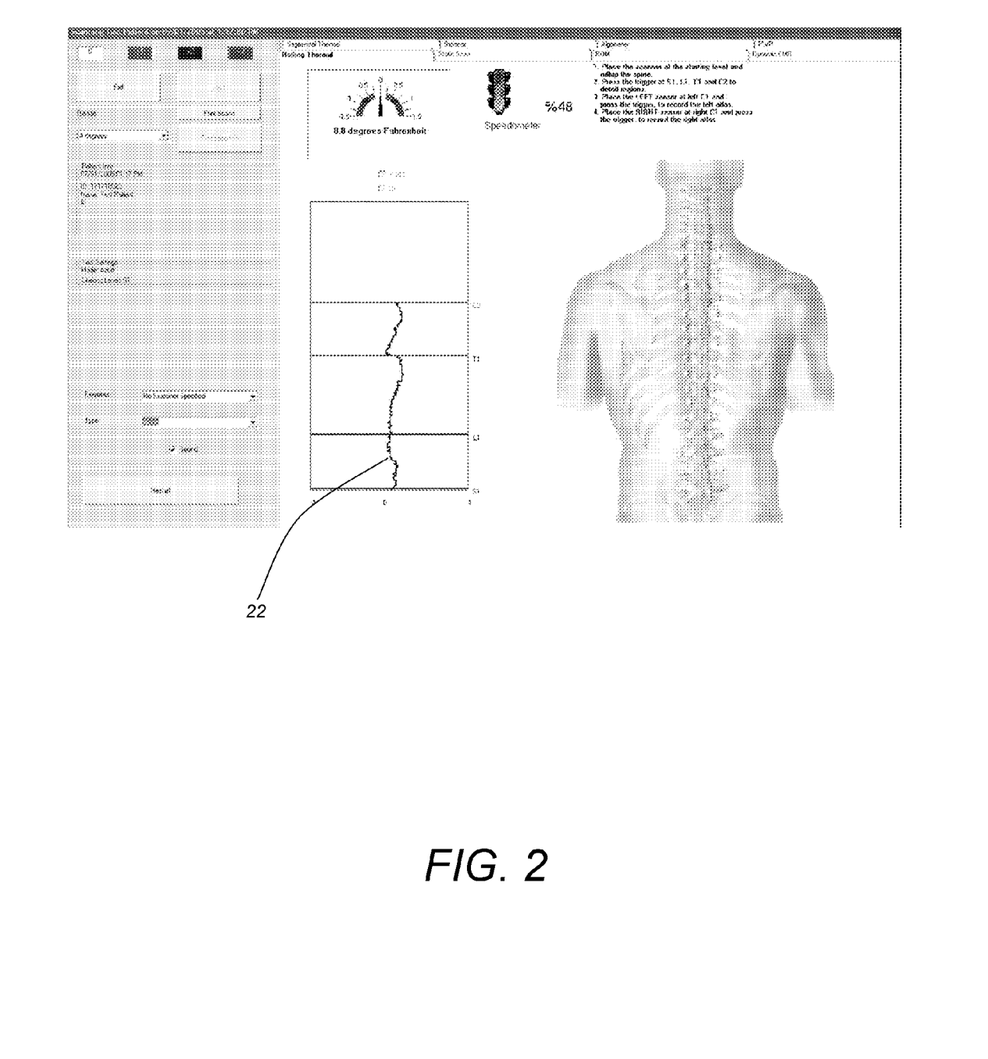
FIG. 2 illustrates an exemplary user display in which differences between the right and left sensors of a first set of thermal scanning data and are displayed graphically.

As the thermal scanner is rolled up the spine, the thermal sensors detects, and the apparatus records, skin temperature data from each side of the patient's spine. When the top of the spine is reached, step 110 is complete. Step 110 is substantially similar to a standard method for bilateral thermal scanning. FIG. 2 illustrates an exemplary user display in which differences 22 between the right and left sensors of a first set of thermal scanning data are displayed graphically.

In optional step 120, the skin temperature data are analyzed to determine whether or not the thermal scan has a one-sided bias, which may indicate miscalibration. In some embodiments, the analysis comprises calculating an average left sensor temperature and an average right sensor temperature for the first set of thermal scanning data collected in step 110. A typical rolling thermal scanner produces several hundred data pairs for a full spine, so in some embodiments, the average value represents an aggregation of several hundred data pairs.

Figure 3:
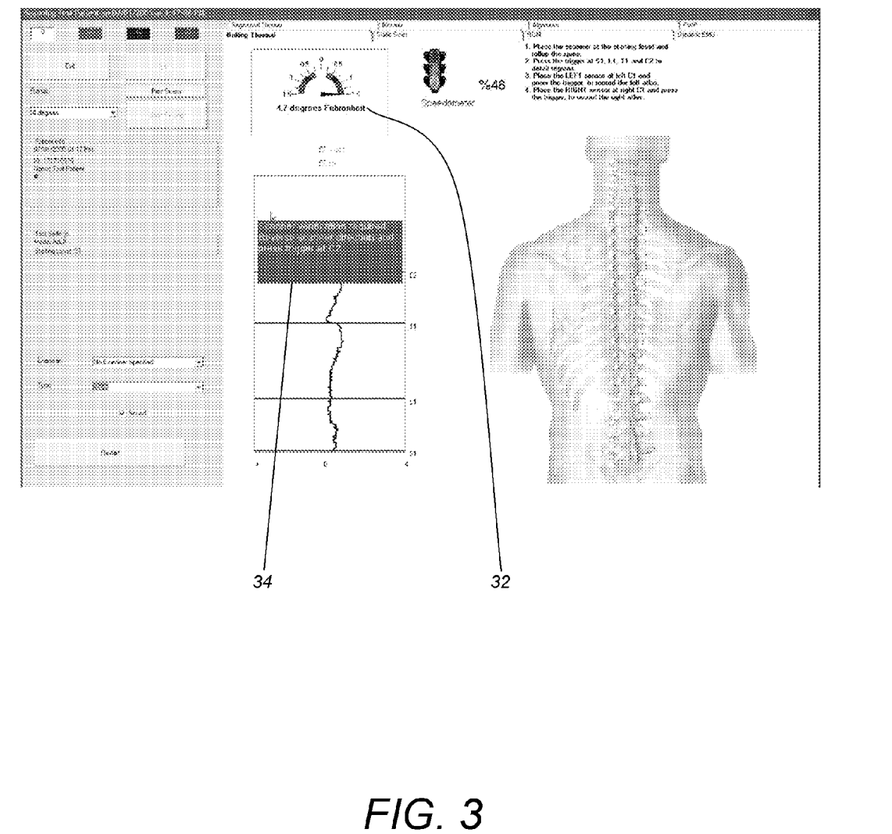
FIG. 3 illustrates an exemplary user display indicating an average temperature bias of 4.7° F.

In some embodiments, a predetermined temperature difference threshold between the average left sensor temperature and the average right sensor temperature is set. If this threshold is exceeded, the calibration procedure is initiated. For example, in some embodiments, a calibration is initiated at a predetermined temperature difference threshold, for example, 0.5 Fahrenheit. FIG. 3 illustrates an exemplary user display indicating an average temperature bias of 4.7° F. 32. In some embodiments, if the temperature difference threshold is not met, the examination of the patient is complete.

Figure 4:
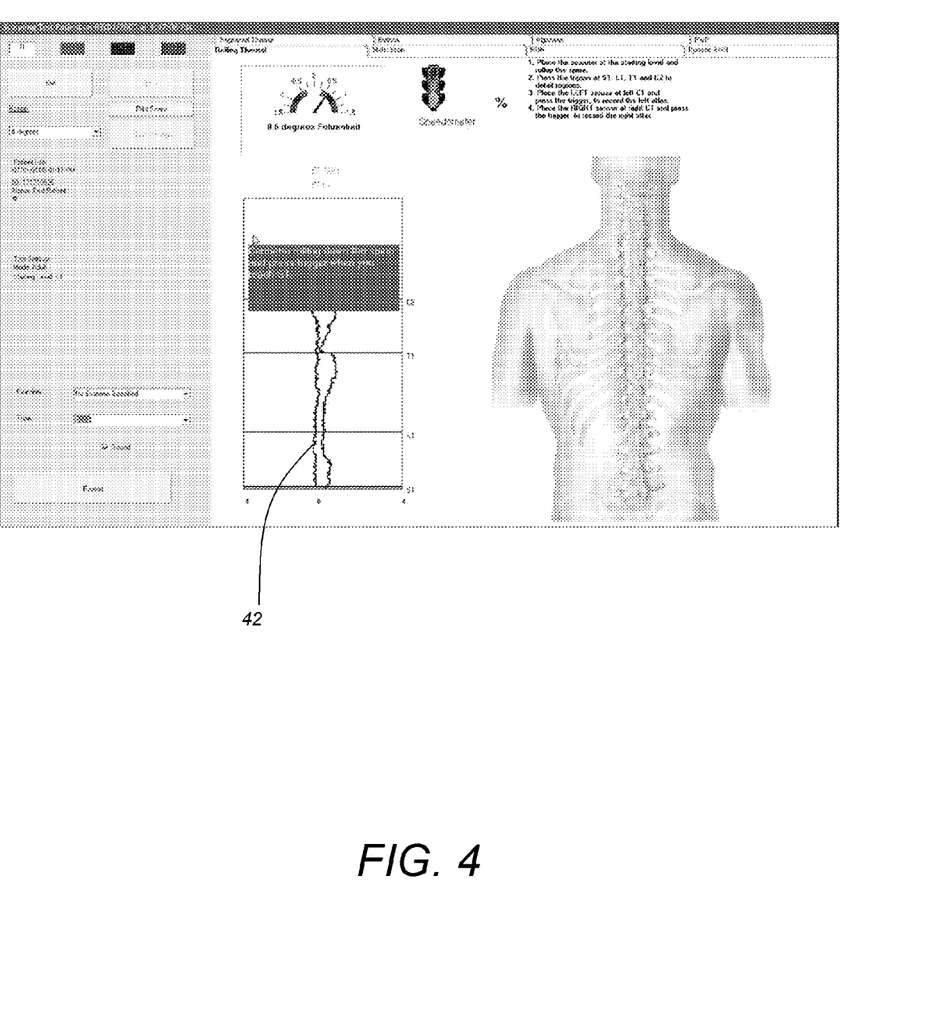
FIG. 4 illustrates an exemplary user display in which differences between the right and left sensors of a second set of thermal scanning data and are displayed graphically.

In step 130, the user is prompted to perform a calibration test if a one-sided bias is detected in step 120. In the embodiment illustrated in FIG. 3, the user is instructed to initiate the calibration or scanner verification procedure 34. In some embodiments, the calibration test comprises turning the thermal scanner upside down so that the left thermal sensor is proximal to the right side of the patient's spine and the right thermal sensor is proximal to the left side of the patient's spine, and positioning the thermal scanner at the top of the spine. The thermal scanner is then rolled down to the base of the spine, thereby acquiring a second set of thermal scanning data. This scan is also referred to as a "calibration scan." In other embodiments, the thermal scanner is turned upside down, thereby interchanging the positions of the first and second thermal sensors, and the calibration scan is performed in the same direction as the scan performed in step 110. FIG. 4 illustrates an exemplary user display in which differences 42 between the right and left sensors of a second set of thermal scanning data are displayed graphically.

In step 140, the average left sensor temperature and average right sensor temperature values are calculated for the second set of thermal scanning data. The thermal sensors' positions are reversed between the first scan and the second scan thereby permitting the user to determine if the first and second thermal sensor channels are balanced. As discussed above, in some embodiments, several hundred data pairs are collected in the first thermal scan, and another several hundred data pairs are collected in the second or calibration or scan. Through calculation, it can be determined if the temperature imbalance was caused by: (1) calibration differences between the infrared thermal sensors, (2) bilateral differences in skin temperature of the patient, or (3) a combination of both. In some embodiments, if no calibration differences are found, the examination of the patient is complete.

In step 150, calibration values are determined if it is determined if calibration differences are found in step 140. In some embodiments, the calibration values are coefficients in one or more formulas applied to one or both of the first and/or second sets of thermal calibration data. In some embodiments, the calibration is applied to the output of one or both of the first and second thermal sensors. For example, in some embodiments, a linear calibration function is used. In these embodiments, the calibration values include at least one of an offset value and a gain value, preferably, at least one offset value and at least one gain value. Other embodiments use another type of calibration function. Still other embodiments do not use a calibration function and determine the calibration values empirically. In embodiments using hundreds of data points, the law of large numbers results in a more accurate and repeatable calibration.

Figure 5:
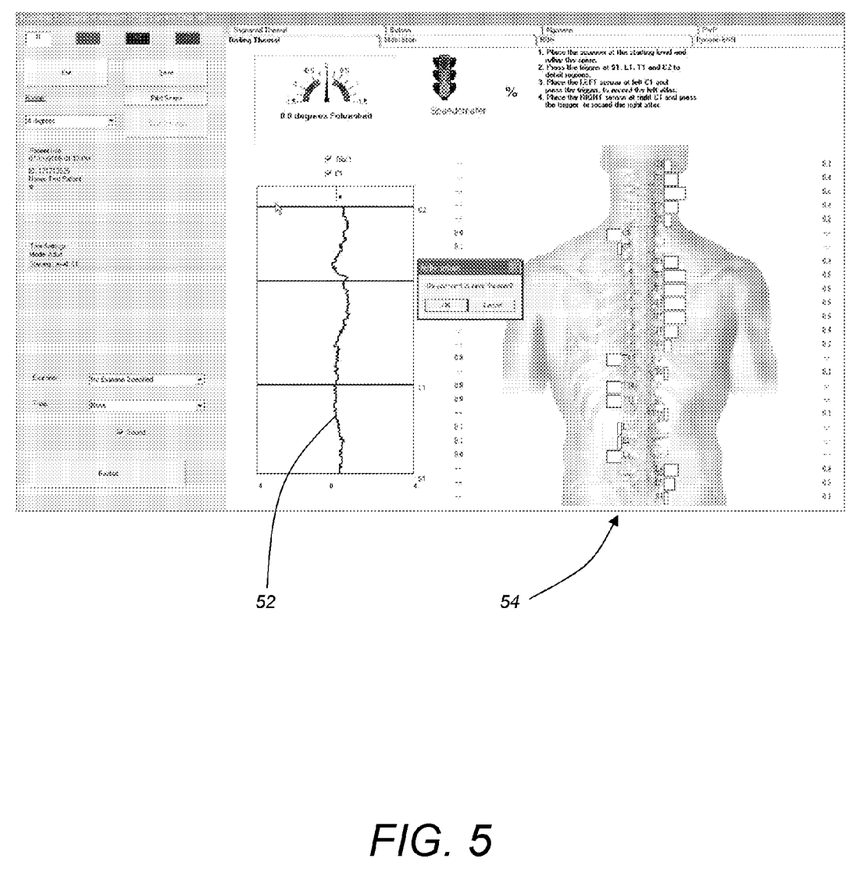
FIG. 5 illustrates an exemplary user display in which corrected thermal scan data are displayed as in FIGS. 2-4, as well as a histogram.

In step 160, the calibration values determined in step 150 are stored, for example, with reference to a particular bilateral thermal scanner. In step 170, at least one of the first and/or second set of thermal scanning data is corrected using the calibration values. FIG. 5 illustrates an exemplary user display in which corrected thermal scan data are displayed graphically 52 as in FIGS. 2-4, as well as a histogram 54 overlaid on an image of a human spine. In some embodiments, the corrected data is updated into a patient record. Optionally, the stored calibration values are applied to one or more subsequent scans.

EXAMPLE

The following example describes a particular embodiment of a method for calibrating an Insight Millennium Rolling Thermal Scanner. Those skilled in the art will understand that other embodiments use other calibration methods and/or devices.

The Rolling Thermal Scanner is rolled up the spine in an upward scan, collecting a first set of thermal scanning data. As the scanner rolls up the spine, an UpLeftAvgTemp (average temperature of the left thermal sensor on the upward scan) and an UpRightAvgTemp (average temperature of the right thermal sensor on the upward scan) values are also calculated. For each thermal sensor, these values are rolling averages of (Temp−CaseTemp) for each data point except the C1 values, where "Temp" is the temperature recorded by a thermal sensor and "CaseTemp" is the temperature of the rolling scanner. The Rolling Thermal Scanner is equipped with a thermal sensor that reports the temperature of the scanner itself (CaseTemp), which permits the conversion of the left and right thermal sensor data into absolute temperatures. The C1 value is omitted from the analysis in this example for reasons of convenience, but those skilled in the art will understand that different startpoints and/or endpoints are used in other embodiments.

$$UpLeftAvgTemp=Avg(Left\ IR\ Temps-CaseTemps)$$

$$UpRightAvgTemp=Avg(Right\ IR\ Temps-CaseTemps)$$

Note that in this example, UpLeftAvgTemp and UpRightAvgTemp incorporate left and right sync values stored in the registry settings. The "sync" values are the calibration values for the left and right thermal sensors. In the current example, the "sync" values are gain values for each thermal sensor.

If UpLeftAvgTemp and UpRightAvgTemp differ by a user-selectable threshold (Thresh), the data are deemed to have a one-sided bias and the calibration procedure is initiated. In other words, the Absolute value of UpLeftAvgTemp−UpRightAvgTemp>Thresh.

In this Example, the second or calibration thermal scan is referred to as a "Reverse Rolling stage." In the Reverse Rolling stage, the user is prompted to invert the scanner, and roll the scanner back down the spine. The Rolling Scanner comprises a trigger for initiating and terminating data acquisition. Clicking the trigger at C2 begins acquiring data. The Rolling Scanner is then rolled down the spine to the Scan starting level (typically, the base of the spine) and the trigger clicked again to terminate data acquisition.

During Reverse Rolling stage, DownLeftAvgTemp (average temperature of the left thermal sensor on the downward scan) and DownRightAvgTemp (average temperature of the right thermal sensor on the downward scan) are calculated as follows:

$$DownLeftAvgTemp=Avg(Left\ IR\ Temps-CaseTemps)$$

$$DownRightAvgTemp=Avg(Right\ IR\ Temps-CaseTemps)$$

Note that in this example, DownLeftAvgTemp and DownRightAvgTemp incorporate the left and right sync values stored in the registry settings.

The old left and right sync values are then removed from the calculations:

$$UpLeft=(UpLeftAvgTemp)/(OldLeftSync)$$

$$UpRight=(UpRightAvgTemp)/(OldRightSync)$$

$$DownLeft=(DownLeftAvgTemp)/(OldLeftSync)$$

$$DownRight=(DownRightAvgTemp)/(OldRightSync)$$

The following equation provides a scale factor, which is the multiplier for properly synced averages on the reverse or downward scan:

$$Scale=SQRT((UpLeft+UpRight)/(DownLeft+DownRight))$$

The ratio of (NewLeftSync)/(NewRightSync) is provided by the following equation:

$$(NewLeftSync)/(NewRightSync)=(Scale)*(DownRight)/(UpLeft)$$

The following three equations can be used to solve for the ratio of (NewLeftSync)/(NewRightSync):

First, the two averages up are set to equal the two averages down, multiplied by new sync values and by the scale factor. The scale factor accounts for imperfections in the performance of the scans.

$$(NewLeftSync)*(UpLeft)+(NewRightSync)*(UpRight)=(Scale)*[(NewLeftSync)*(DownLeft)+(NewRightSync)*(DownRight)]$$

Second, the upward and downward scans of left side of the body are set to a constant average temperature:

$$(NewLeftSync)*(UpLeft)=(NewRightSync)*(Scale)*(DownRight)$$

Third, the upward and downward scans of the right side of the body are set to a constant average temperature:

$$(NewRightSync)*(UpRight)=(NewLeftSync)*(Scale)*(DownLeft)$$

For convenience, if the ratio NewLeftSync/NewRightSync≧1 then:

NewRightSync=1 and

NewLeftSync=NewLeftSync/NewRightSync

If NewLeftSync/NewRightSync<1 then:

NewLeftSync=1 and

NewRightSync=NewRightSync/NewLeftSync

The new sync values are then saved to the registry files. In some embodiments, the upward, downward, or both scan data recalculated using the new sync values, and the recalculated data stored in a database. This example is generalizable to adult, child and infant modes.

Although these inventions have been disclosed in the context of certain preferred embodiments and examples, it will be understood by those skilled in the art that the present inventions extend beyond the specifically disclosed embodiments to other alternative embodiments and/or uses of the inventions and obvious modifications and equivalents thereof. In addition, while several variations of the inventions have been shown and described in detail, other modifications, which are within the scope of these inventions, will be readily apparent to those of skill in the art based upon this disclosure. It is also contemplated that various combination or sub-combinations of the specific features and aspects of the embodiments may be made and still fall within the scope of the inventions. It should be understood that various features and aspects of the disclosed embodiments can be combined with or substituted for one another in order to form varying modes of the disclosed inventions. Thus, it is intended that the scope of at least some of the present inventions herein disclosed should not be limited by the particular disclosed embodiments described above.

What is claimed is:

1. A method for calibrating a bilateral thermal scanner, the method comprising:
   acquiring, with the bilateral thermal scanner comprising a first thermal sensor and a second thermal sensor, a first set of bilateral temperature data using the first thermal sensor and the second thermal sensor;
   acquiring a second set of bilateral temperature data, wherein the positions of the first thermal sensor and second thermal sensor are substantially interchanged from their position when acquiring the first set of bilateral temperature data; and
   comparing the first and second sets of bilateral temperature data to determine at least one calibration value for the bilateral thermal scanner.

2. The method of claim 1, wherein the acquiring steps involve rolling the bilateral thermal scanner over a surface.

3. The method of claim 1, wherein the acquiring steps involve placing the first and second thermal sensors, which are operable to determine temperature, against a surface.

4. The method of claim 1, additionally comprising activating a component of the bilateral thermal scanner to initiate data acquisition.

5. The method of claim 1, wherein the acquiring steps involve placing the first and second thermal sensors to collect thermal data from opposite sides of a patient's spine.

6. The method of claim 1, wherein the acquiring steps involve sensing the intensity of radiation from a surface.

7. The method of claim 1, additionally comprising displaying at least some of the acquired first and second sets of bilateral temperature data.

8. The method of claim 1, further comprising determining whether the first set of bilateral temperature data has a one-sided bias.

9. The method of claim 8, wherein determining whether the first set of bilateral temperature data has a one-sided bias comprises calculating a difference between an average of temperature data from the first thermal sensor and an average of temperature data from the second thermal sensor.

10. The method of claim 8 additionally comprising prompting a user to perform a calibration test if the one-sided bias is greater than a predetermined value.

11. The method of claim 1, wherein
   one of acquiring a first set of bilateral temperature data and acquiring a second set of bilateral temperature data comprises scanning up a patient's spine, and
   the other of acquiring a first set of bilateral temperature data and acquiring a second set of bilateral temperature data comprises scanning down a patient's spine.

12. The method of claim 1, wherein the at least one calibration value comprises at least one of a gain and an offset.

13. The method of claim 1, further comprising applying the at least one calibration value to at least one of the first and second sets bilateral temperature data.

14. The method of claim 1, further comprising applying the at least one calibration value to the output of at least one of the first and second thermal sensors.

15. The method of claim 1, further comprising saving the at least one calibration value.

16. The method of claim 15, wherein the at least one calibration value is applied to subsequent sets of first and second bilateral temperature data.

17. A method for performing a bilateral temperature measurement using a bilateral thermal scanner comprising a first thermal sensor and a second thermal sensor, the method comprising:
   acquiring a first set of bilateral the temperature data using bilateral thermal scanner;
   acquiring a second set of bilateral temperature data using the bilateral scanner, wherein the positions of the first thermal sensor and second thermal sensor are substantially interchanged from their position when acquiring the first set of bilateral temperature data; and
   calculating a bilateral temperature measurement from the first and second sets of bilateral temperature data.

18. A system for calibrating a bilateral thermal scanner comprising:
   a bilateral thermal scanner comprising a first thermal sensor and a second thermal sensor;
   a display;
   a data processing unit coupled to the bilateral thermal scanner and the display; and
   machine readable instructions, which when executed by the data processing unit calibrate the bilateral thermal scanner by a method comprising:
      comparing a first set of bilateral temperature data and a second set of bilateral temperature data obtained by the bilateral thermal scanner to determine at least one calibration value for the bilateral thermal scanner,
      wherein the positions of the first thermal sensor and the second thermal sensor are substantially interchanged between acquiring the first set of bilateral temperature data and the second set of bilateral temperature data.

* * * * *

UNITED STATES PATENT AND TRADEMARK OFFICE
CERTIFICATE OF CORRECTION

PATENT NO. : 7,438,466 B1
APPLICATION NO. : 11/615875
DATED : October 21, 2008
INVENTOR(S) : Gentempo, Jr. et al.

It is certified that error appears in the above-identified patent and that said Letters Patent is hereby corrected as shown below:

Column 10, line 24, in Claim 13, after "sets" insert therefore, -- of --.

Column 10, line 37, in Claim 17, after "bilateral" delete therefore, "the".

Column 10, line 38, in Claim 17, before "bilateral" insert therefore, -- a --.

Column 10, line 41, in Claim 17, after "bilateral" insert therefore, -- thermal --.

Signed and Sealed this

Fifteenth Day of June, 2010

David J. Kappos
*Director of the United States Patent and Trademark Office*